US00PP14055P39

(12) United States Plant Patent
Vijverberg

(10) Patent No.: US PP14,055 P3
(45) Date of Patent: Aug. 12, 2003

(54) CHRYSANTHEMUM PLANT NAMED 'VYKING ORANGE DARK'

(75) Inventor: Arnold Vijverberg, 's-Gravenzande (NL)

(73) Assignee: Vyking Flowers B.V. (NL)

( * ) Notice: Subject to any disclaimer, the term of this patent is extended or adjusted under 35 U.S.C. 154(b) by 353 days.

(21) Appl. No.: 09/757,634

(22) Filed: Jan. 11, 2001

(65) Prior Publication Data

US 2002/0129417 P1 Sep. 12, 2002

(51) Int. Cl.[7] ..... A01H 5/00

(52) U.S. Cl. ..... Plt./296

(58) Field of Search ..... Plt./296

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'Vyking Orange Dark' characterized by its small sized blooms with orange ray-florets and brown disc florets.

3 Drawing Sheets

RELATED CULTIVARS

'VYKING ORANGE DARK' is related to 'VYKING' (Ser. No. 09/708,588). 'VYKING ORANGE DARK' is a sport of 'VYKING'.

BACKGROUND OF THE INVENTION

'VYKING ORANGE DARK' is a product of a breeding and selection program which had the objective of finding color mutants of 'VYKING'. The new plant of the present invention comprises a new and distinct cultivar of chrysanthemum plant that is a natural occuring sport of a parent chrysanthemum named 'VYKING'. A comparison with parent chrysanthemum 'VYKING' is also made in this application. The new cultivar was discovered as a sport in April 1999 by Arnold Vijverberg in a controlled environment (greenhouse) in 's-Gravenzande, Holland. The first act of asexual reproduction of 'VYKING ORANGE DARK' was accomplished when vegetative cuttings were taken from the initial selection in June 1999 in 's-Gravenzande, Holland.

SUMMARY OF THE INVENTION

The present invention is a new and distinct variety of chrysanthemum bearing small sized blooms with orange ray-florets and brown disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
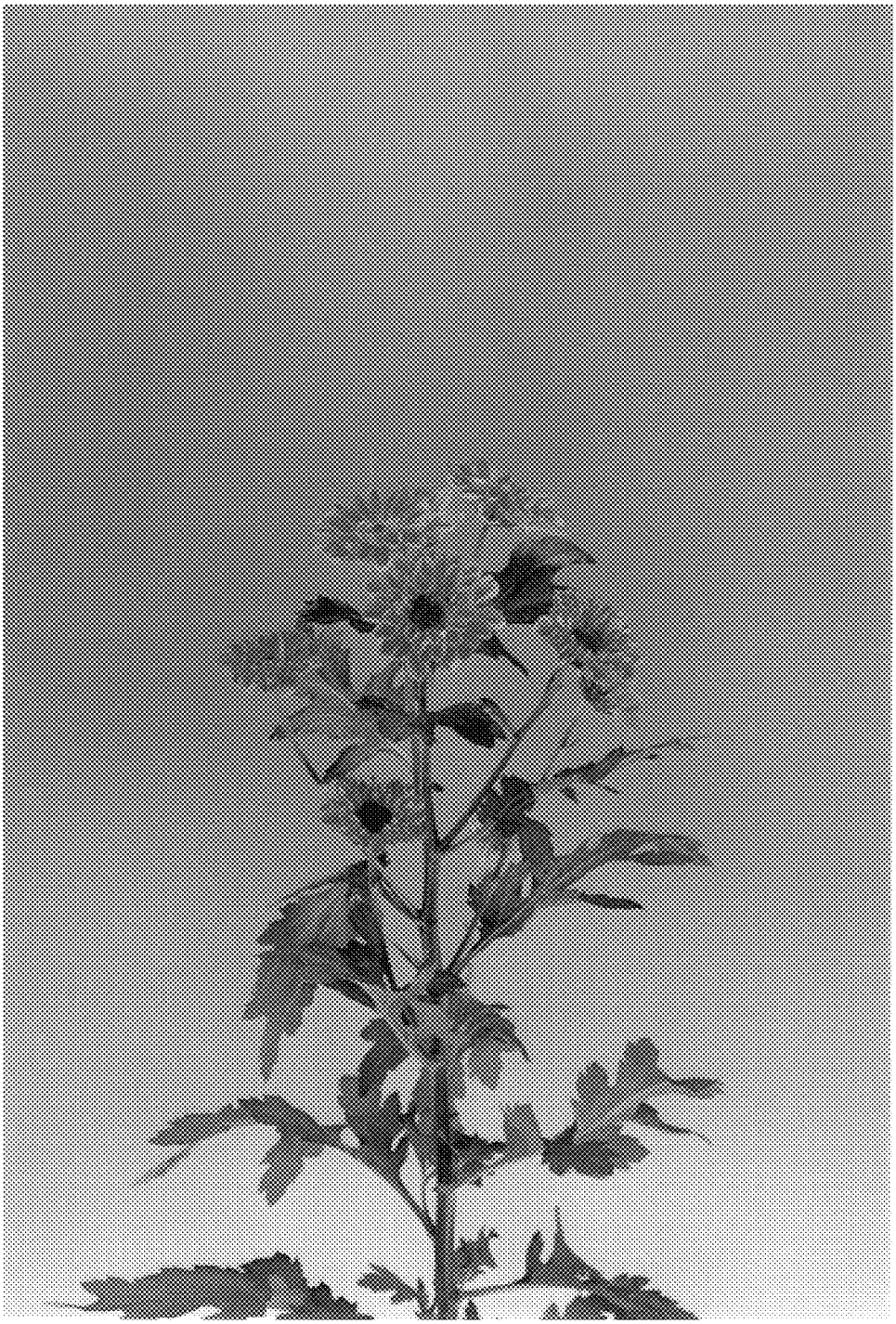
FIG. 1 shows a plant of the cultivar in full bloom.
Figure 2:
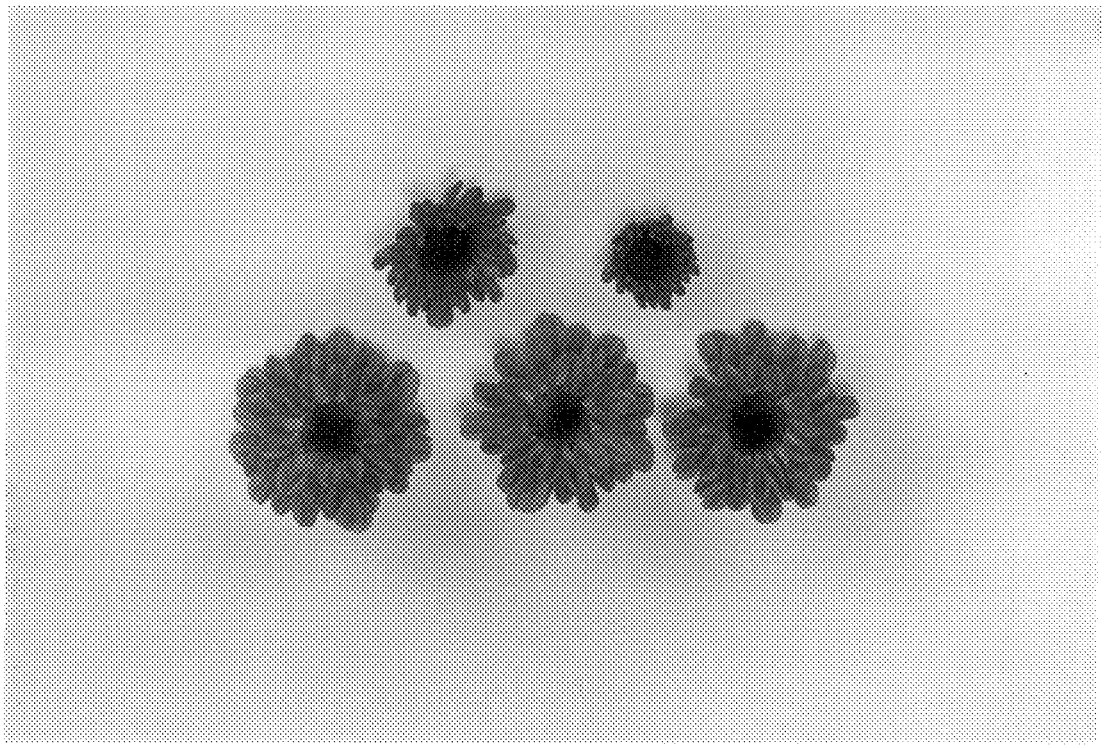
FIG. 2 shows the various stages of bloom of the new cultivar.
Figure 3:
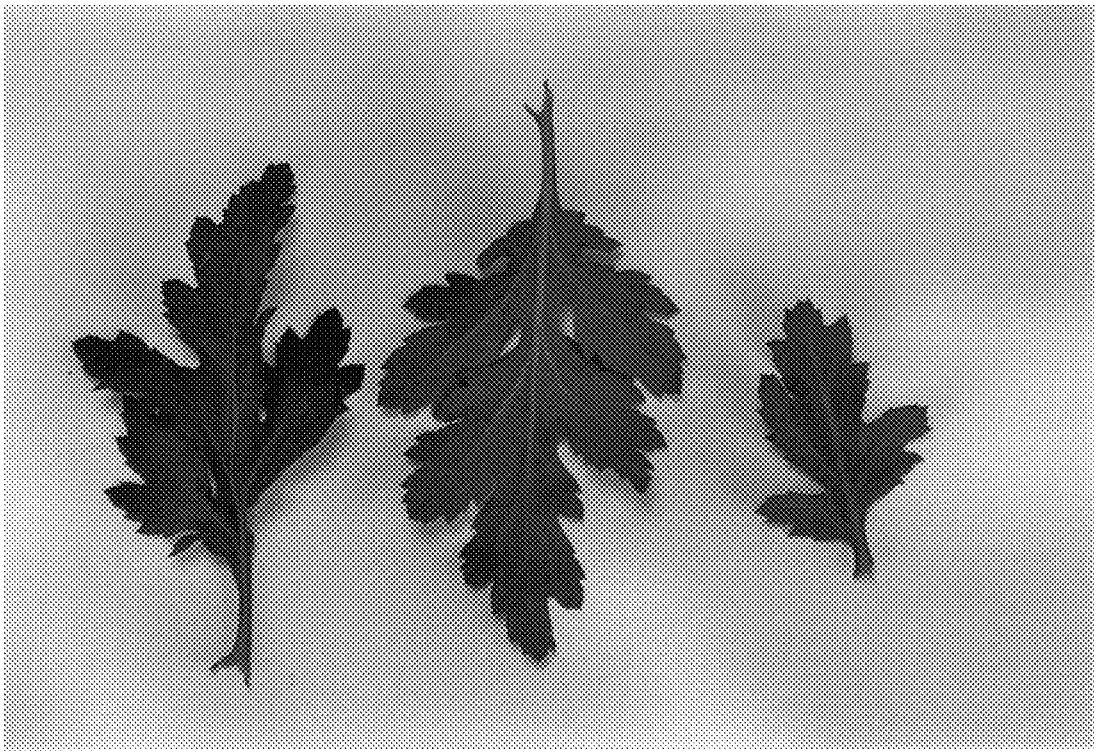
FIG. 3 shows the foliage of the new cultivar.

This new variety of chrysanthemum is of the botanical classification *Chrysanthemum morifolium*. The observations and measurements were gathered from plants grown in April/May in a greenhouse in 's-Gravenzande, Holland in a photo-periodic controlled crop under conditions generally used in commercial practice. The greenhouse temperatures during this crop were at a day-time between 18° C. and 25° C. and at night 20° C. After a long day period of 14 days, the photo-periodic response time in this crop was 52 days. After the long day period to flowering, growth retardants were applied 2 to 3 times in an average dose of 2.5 gram/liter water. No tests were done on disease or insect resistance or susceptibility. No tests were done on cold or drought resistance. This new variety produces small sized blooms with orange ray-florets and brown disc-florets blooming on the plant for 3 weeks. This new variety of chrysanthemum has been found to retain its distinctive characteristics throughout successive propagations; however, the phenotype may vary significantly with variations in environment such as light intensity and temperature. To show the phenotype as described 'VYKING ORANE DARK' can be planted without assimilation lighting (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivars in comparison to 'VYKING ORANGE DARK' are 'VYKING' and 'VYMINI' (U.S. Plant Pat. No. 11,627). 'VYKING ORANGE DARK' is a natural mutant of 'VYKING'. When 'VYKING' and 'VYKING ORANGE DARK' are being compared the following differences and similarities are noticed: The difference of 'VYKING' and 'VYKING ORANGE DARK' are (1): flower color and (2) flower form. (3) Response time. All other characteristics of 'VYKING' and 'VYKING ORANGE DARK' are the same. (1) Flower color: 'VYKING ORANGE DARK' is a color mutant of 'VYKING' bearing orange blooms instead of yellow blooms. (2) Flower form: The ray florets of 'VYKING ORANGE DARK' are more folded and more concave as the ray florets of 'VYKING'. (3) Response time. The response time of 'VYKING ORANGE DARK' is 52 days, 'VYKING' has a response time of 56 days.

When 'VYMINI' and 'VYKING ORANGE DARK' are being compared the following differences are noticed: The differences of 'VYMINI' and 'VYKING ORANGE DARK' are: (1) flower color, (2) flower size and (3) leaf size. (1) Flower color. 'VYKING ORANGE DARK' has orange colored ray-florets, 'VYMINI' has yellow colored ray-florets. (2) Flower size. The size of the flowers of 'VYKING ORANGE DARK' is larger. (3) Leaf size. The size of the leaves of 'VYKING ORANGE DARK' is larger.

The following is a description of the plant and characteristics that distinguish 'VYKING ORANGE DARK' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Botanical Description of Cultivar 'VYKING ORANGE DARK'

Bud:

*Size.*—Medium, cross-section 1.5 cm height 1.2 cm.

*Outside color.*—Greyed-orange 169D.

*Involucral bracts.*—2 rows, length 7 mm, width 3 mm.

*Involucral bracts among disc-florets.*—Not present.

*Involucral bracts color.*—Yellow-green 146 A.

Bloom:

*Type.*—Single.

*Height.*—Low, 1.3–1.7 cm.

*Size.*—Small.

*Fully expanded.*—4–5 cm.

*Number of blooms per stem.*—Average of 8.

*Performance on the plant.*—21 days.

*Seeds* (*if crossed*).—Produced in small quantities, ovate shaped. Grey-brown 199 A, 2 mm in length.

*Fragrance.*—Typical chrysanthemum, slight.

Color:

*Center of the flower* (*disc-florets*).—Immature greyed-orange 166A. Mature greyed-orange 165 A.

*Color of upper surface of the ray-florets.*—Greyed-orange 169C.

*Color of the lower surface of the ray-florets.*—Greyed-orange 169D.

*Tonality from distance.*—A spray mum with orange flowers and a brown disc.

*Color of the upper surface of the ray-florets after aging of the plant.*—Greyed-orange 169D.

Ray florets:

*Texture.*—Upper and under side smooth.

*Number.*—55–65, three rows.

*Cross-section.*—Concave, one keel.

*Longitudinal axis of majority.*—Straight to incurved.

*Length of corolla tube.*—Short, 0.4–0.6 cm.

*Ray-floret margin.*—Entire.

*Ray-floret.*—1.5–2.0 cm.

*Ray-floret width.*—0.5–0.7 cm.

*Ratio length/width.*—Medium.

*Shape of tip.*—Rounded, sometimes dentate.

Disc florets:

*Disc diameter.*—1.5 cm.

*Distribution of disc florets.*—Numerous clearly visible at all stages of flowering.

*Shape.*—Tubular.

*Color.*—Yellow-green 144 A, greyed-orange 166 A at the tip.

*Receptacle shape.*—Conical raised.

Reproductive organs:

*Stamen* (*present in disc florets only*).—Thick, 4 mm in length.

*Number of stamen.*—4.

*Stamen color.*—Yellow-green 144 A.

*Pollen.*—Not present.

*Styles* (*present in ray-and disc-florets*).—Thick.

*Style color.*—Yellow-green 144 A.

*Style length.*—5 mm.

*Stigmas.*—Yellow-green 144 A.

*Stigma width.*—1 mm.

*Ovaries.*—Enclosed in calyx.

Plant:

*Form.*—A spray mum meant for erect culture.

*Growth habit.*—Upright.

*Growth rate.*—Slow.

*Height.*—100 cm.

*Width.*—16 cm.

*Internodes.*—2.5–3.0 cm.

*Spray formation.*—Corymbiform.

*Stem color.*—Yellow-green 146 A.

*Stem strength.*—Strong.

*Stem brittleness.*—Present.

*Stem anthocyanin coloration.*—Present, a thin layer of greyed-red 181 A mainly at the base of the stem.

*Peduncle length.*—Near the top 6 cm, near the middle 12 cm, near the bottom 16 cm.

*Peduncle color.*—Yellow-green 146 A.

*Petiole length.*—1.5–2 cm.

*Petiole color.*—Yellow-green 145C.

*Rib and vein color upperside leaves.*—Yellow-green 145C.

*Rib and vein color underside leaves.*—Yellow-green 148C.

*Flowering response* (*photo-periodic controlled crop*).—52 days.

Foliage:

*Color mature.*—Upper side yellow-green 147 A. Under side yellow-green 147 B.

*Color immature.*—Upper side yellow-green 146 A. Under side yellow-green 146 B.

*Size.*—Large; length 12 cm, width 7 cm.

*Quantity* (*number per single stem*).—30–32.

*Shape.*—Ovate.

*Texture upper side.*—Fleshy and glabrous.

*Texture under side.*—Pubescent.

*Venation arrangement.*—Palmate.

*Shape of the margin.*—Crenated.

*Shape of base of sinus between lateral lobes.*—Round.

*Margin of sinus between lateral lobes.*—Converging.

*Shape of base.*—Truncate.

*Apex.*—Mucronate.

TABLE 2

| | Differences with the comparison Varieties | | |
|---|---|---|---|
| | 'VYKING ORANGE DARK' | 'VYKING' | 'VYMINI' |
| Color of ray-florets | Greyed-orange 169 C | Yellow 12 A | Yellow 7 B |
| Size bloom | Medium | Medium | Small |
| Size leaves | Medium | Medium | Small |
| Response time | 52 days | 56 days | 45 days |

I claim:

1. A new and distinct variety of chrysanthemum plant as described and illustrated.

* * * * *